United States Patent [19]
Arter et al.

[11] Patent Number: 5,981,206
[45] Date of Patent: Nov. 9, 1999

[54] DRY ANALYTICAL ELEMENT AND METHOD FOR THE DETECTION OF PROSTATIC ACID PHOSPHATASE

[75] Inventors: Thomas Charles Arter, Rochester; Mohan S Saini, Pittsford, both of N.Y.

[73] Assignee: Johnson & Johnson Clinical Diagnostic Systems, Inc., Rochester, N.Y.

[21] Appl. No.: 07/886,263

[22] Filed: May 20, 1992

[51] Int. Cl.⁶ .............................. C12Q 1/42; C12Q 1/00
[52] U.S. Cl. ........................ 435/21; 435/4; 435/283.1; 435/287.1; 435/287.7; 435/287.8
[58] Field of Search .................... 435/21, 15, 28, 435/13, 11, 7.72, 4, 5, 7.5, 283.1, 287.1, 287.7, 287.8

[56] References Cited

U.S. PATENT DOCUMENTS

| | | | |
|---|---|---|---|
| 3,002,893 | 10/1961 | Babson | 195/103.5 |
| 3,410,756 | 11/1968 | Gullbault et al. | 195/103.5 |
| 3,595,756 | 7/1971 | Steciw | 435/19 |
| 3,905,872 | 9/1975 | Forgione et al. | 195/103.5 R |
| 3,992,158 | 11/1976 | Przybylowicz | 435/11 |
| 4,042,335 | 8/1977 | Clement | 435/13 |
| 4,162,194 | 7/1979 | Pierre et al. | 435/15 |
| 4,510,239 | 4/1985 | Miller et al. | 435/7 |
| 4,547,460 | 10/1985 | Eikenberry | 435/15 |
| 4,555,484 | 11/1985 | LaRossa et al. | 435/21 |
| 4,681,841 | 7/1987 | Matsumoto et al. | 435/18 |
| 4,758,508 | 7/1988 | Schnabel et al. | 435/19 |
| 4,806,470 | 2/1989 | Frickey et al. | 435/21 |
| 4,868,106 | 9/1989 | Ito et al. | 435/7.5 |
| 4,892,817 | 1/1990 | Pawlak | 435/21 |
| 4,900,665 | 2/1990 | Terashima et al. | 435/21 |
| 4,956,146 | 9/1990 | Yuhki et al. | 435/28 |
| 4,966,856 | 10/1990 | Ito et al. | 435/4 |
| 4,983,512 | 1/1991 | Teshima et al. | 435/21 |
| 5,077,011 | 12/1991 | Amano et al. | 435/21 |
| 5,081,274 | 1/1992 | Kuroiwa et al. | 558/198 |

FOREIGN PATENT DOCUMENTS

| | | |
|---|---|---|
| 2115748 | 7/1980 | Germany . |
| 1/197493 | 1/1988 | Japan . |
| 3-088000 | 4/1988 | Japan . |
| 63-88000 | 4/1988 | Japan . |
| 1/257265 | 10/1989 | Japan . |
| 2095832 | 10/1982 | United Kingdom . |
| WO 83/03254 | 9/1983 | WIPO . |
| WO 90/10084 | 9/1990 | WIPO . |

OTHER PUBLICATIONS

Escribano et al; Biochem J. (1984) vol. 223, p633–638.
Sanders et al; Clinica Chimica Acta, vol. 89 (1978) p421–427.
Cooper et al; Clinica Chemica Acta, vol. 126 (1982) p297–306.
Pernicova, Marie; Chemical Abstracts 76(23):137678r (1971).
Katsuyama, Shunkai; Chemical Abstracts 110(25):227739m (1988).
Babson et al, Am.J.Clin.Path. 32, pp. 88–91 (1959).
Buchwald et al, *J.Biol.Chem.*, 259(4), pp. 2208–2213. (1984).
Huggins et al, *J.Biol.Chem.*, 159, pp. 399–410 (1945).
Hillmann, Z. Klinischen Chemie und Klinischen Biochemie, 9(3), pp. 273–274, 1971 and English translation.

*Primary Examiner*—Louise N. Leary

[57] ABSTRACT

A dry analytical element has been prepared for the assay of prostatic acid phosphatase at a pH of from about 3 to about 6.5. The element can be a single porous spreading zone or a multilayer structure. Within the element is a relatively nonhygroscopic aromatic phosphate substrate for the analyte which produces a phenol reaction product. This product is reacted with a diazonium or tetrazolium salt, also in the element, to produce a chromophore for detection. A buffer in the element maintains it at the proper pH during the assay.

18 Claims, No Drawings

DRY ANALYTICAL ELEMENT AND METHOD FOR THE DETECTION OF PROSTATIC ACID PHOSPHATASE

FIELD OF THE INVENTION

The present invention relates to clinical chemistry. In particular, it relates to an analytical element and method for the determination of prostatic acid phosphatase in aqueous specimens, such as biological fluids.

BACKGROUND OF THE INVENTION

Prostatic acid phosphatase (PAP) is also known as orthophosphoric monoester phosphohydrolase, acid optimum, E.C. 3.1.3.2., and is a glycoprotein of about 100,000 daltons molecular weight normally found in the prostate gland. It is a major constituent of semen. It is also present in serum at low levels, and is normally a mixture of enzymes contributed by various tissues in the human body.

Assays for PAP began to be important several decades ago when it was discovered that serum acid phosphatase activity becomes elevated when metastatic cancer of the prostate or prostatomegaly is present. Thus, a determination of the amount of PAP in body fluids can be useful for the diagnosis of such diseases and for the observation of their progress or remission. Various spectrophotometric assays have been developed using immunological and non-immunological techniques and various enzyme substrates and dyes. Typically, PAP is evaluated from the amount or rate of formation of a chromophore (such as a dye). The chromophore is a coupled product of a phenol, resulting from the enzymatic hydrolysis of phospho monoester with, for example, a diazonium dye in an acidic environment.

A representative early assay for PAP is described in U.S. Pat. No. 3,002,893 (Babson). Another described by Babson et al in *Am.J.Clin.Pathol.*, 32, pages 88–91 (1959) suffers from a number of disadvantages such as the need for a blank to be run, lack of kinetic results and difficulty in formulating a dry assay.

Other assays using various phosphate substrates have been developed, but suffer from insensitivity, reagent instability or nonspecificity for the analyte. The most difficult problem is the instability of various reagents which, in a dry element, are stored for lengthy periods of time prior to their use. For example, sodium salts of the PAP substrate are unstable when stored for a period of time.

It would be highly desirable to have an assay for PAP which can be carried out in a dry analytical element which would provide a number of important advantages. To achieve this result, however, requires that a number of technical problems (noted above) be overcome.

SUMMARY OF THE INVENTION

The problems noted above with known assays have been overcome with an analytical element useful for the determination of prostatic acid phosphatase in an aqueous specimen comprising:
a porous spreading zone containing
  (a) a nonhygroscopic aromatic phosphate which reacts as a substrate with prostatic acid phosphatase to produce a phenol reaction product, and
  (b) a diazonium or tetrazolium salt which is capable of reacting with the phenol reaction product to provide a chromophore,
the element further comprising a buffer which maintains the element at a pH of from about 3 to about 6.5 when contacted with an aqueous specimen.

This invention also provides a method for the determination of prostatic acid phosphatase comprising the steps of:
  A) contacting an aqueous specimen suspected of containing prostatic acid phosphatase with the analytical element described above, and
  B) detecting the formation of a chromophore as an indication of the presence of prostatic acid phosphatase in the specimen.

Further, the present invention also provides a method for providing a storage stable analytical element useful for the determination of prostatic acid phosphatase comprising:
  A) applying a reagent layer formulation containing:
    an accelerator, and
    a buffer which maintains the element at a pH of from about 3 to about 6.5 when contacted with an aqueous specimen,
    to a nonporous, transparent support,
  B) applying a subbing layer formulation to the reagent layer, and
  C) applying a porous spreading layer formulation to the subbing layer, the spreading layer containing
    (a) a nonhygroscopic aromatic phosphate substrate for prostatic acid phosphatase which reacts with prostatic acid phosphatase to produce a phenol reaction product, and
    (b) a diazonium or tetrazolium salt which is capable of reacting with the phenol reaction product to provide a chromophore.

The present invention provides a dry analytical element for the effective and specific detection of prostatic acid phosphatase (PAP) in a relatively short period of time at an acidic pH. The reagents in the element are highly stable so the element can be stored for a lengthy period of time before use without loss of activity and sensitivity. These advantages are achieved by using a relatively nonhygroscopic aromatic phosphate substrate for PAP which does not absorb water to an appreciable extent. In a preferred embodiment, the diazonium or tetrazolium salt and buffer used in the assay are kept separated in the element prior to the assay. This further improves storage stability.

DETAILED DESCRIPTION OF THE INVENTION

The present invention relates to a determination (that is, detecting either the presence, amount or both) of PAP. In particular, the invention can be used to assay any aqueous fluid suspected of containing PAP, and particularly biological fluids including, but not limited to, serum, urine, semen, lymph, plasma, whole blood and cerebral spinal fluid. It is also possible to assay fluid preparations of tissue such as preparations of the prostate gland. Preferably, human serum or plasma is assayed with this invention.

In its broadest embodiment, the dry element of this invention has a porous spreading zone (or layer) which is fluid permeable and contains all of the reagents needed for the detection of PAP. Optional materials can be in other optional (yet preferred) zones. The elements are known as test strips, test slides or diagnostic devices. The zone can be "self-supporting", which means that it can be composed of materials which maintain their integrity when exposed to aqueous fluids, such as a filter paper or glass, polymeric or cellulosic membrane. Preferably, however, such a zone is disposed on a separate, nonporous support which is generally dimensionally stable, inert to chemical reaction and preferably transparent (that is, radiation transmissive for wavelengths between about 200 and 900 nm). However, non-transparent supports can be used if the mode of detection is reflectance spectroscopy instead of transmission spectroscopy. Useful supports are well known in the art, and include but not limited to polyesters, papers, metal foils and polystyrene, polycarbonates and cellulose esters.

The porous spreading zone is prepared from any of the known materials used for such zones as described, for example in U.S. Pat. No. 4,292,272 (Kitajima et al), U.S. Pat. No. 3,992,158 (Przybylowicz et al), U.S. Pat. No. 4,258,001 (Pierce et al) U.S. Pat. No. 4,430,436 (Koyama et al) and related U.S. patents, and JP 57(1982)-101760 (published Jun. 24, 1982). It is desired that the spreading zone be isotropically porous, meaning that the porosity is the same in each direction in the zone as caused by interconnected spaces or pores between particles, fibers or polymeric strands.

Preferred spreading zones are those described in U.S. Pat. No. 3,992,158 as "blush polymer" zones. Such zones can be formed on a supporting material by dissolving a polymer in a mixture of two organic liquids, one of which is a lower boiling, good solvent for the polymer and other being a high boiling, non-solvent or poor solvent for the polymer. The resulting polymer formulation is coated on the supporting material and dried under controlled conditions to leave an isotropically porous zone. Various polymers are known to be useful in this context including, but not limited to, polycarbonates, polyamides, polyurethanes and cellulose esters such as cellulose acetate (which is preferred).

Within the porous zone can be incorporated particulate materials of various sizes to enhance the void volume. Useful particulate materials include, but are not limited to, inorganic pigments such as titanium dioxide, barium sulfate, zinc oxide and lead oxide, with barium sulfate being preferred. Further details of the preparation of "blush polymers" are described in U.S. Pat. No. 3,992,158 (noted above).

Preferably, the elements have at least one other zone which can contain one or more reagents needed for the assay. Such a zone is often known in the art as a reagent or registration zone, but it can also include a second porous spreading zone if desired or printed layers located on other zones. The zones are generally in fluid contact with each other, meaning that fluids, reagents and reagent products can pass or be transported between superposed regions of adjacent zones, unless of course, a reagent is immobilized in some manner so it will not migrate within or without a zone. Preferably, the zones are separately coated as superposed layers on an inert support (see Example 1 below). The reagent zones or layers can be composed of one or more binder materials [such as gelatin and other colloidal materials, hydrophilic polymers such as poly(vinyl alcohol), acrylamide polymers, vinylpyrrolidone polymers and others known in the art] in which reagents are incorporated.

The assay of this invention is carried out with the following sequence of reactions at a pH of from about 3 to about 6.5:
  (a) PAP in a specimen is reacted with the nonhygroscopic aromatic phosphate substrate in the element to provide a phenol reaction product, and
  (b) the phenol reaction product is coupled (or reacted) with a diazonium or tetrazolium salt to provide a detectable chromophore.

In an optimized assay, the conditions and amounts of reagents used in step (a) are adjusted so it is the rate limiting step of the assay.

The substrate for the analyte is relatively nonhygroscopic. The substrate is particularly less hygroscopic than substrate having sodium or potassium cations. The substrate is also at least partially water-soluble at the pH used in the assay.

The substrate also contains a phosphate group on an aromatic ring, and the phosphate group is cleaved by PAP to leave a hydroxy group on the ring of the resulting phenol reaction product. By phenol is meant any aryl hydroxide (substituted or unsubstituted) which is derived from any of the substrates described below. Preferably, the substrate is a nonhygroscopic salt of an aryl phosphate ester. Such aryl phosphate esters include, but are not limited to, p-nitrophenyl phosphate, phenolphthalein monophosphate, phenolphthalein diphosphate, thymolphthalein monophosphate, indoxyl phosphate, phenyl phosphate, α-naphthyl phosphate, β-naphthyl phosphate, β-glycerol phosphate acid, o-carboxyphenyl phosphate acid, o-methylfluorescein phosphate, 4-(4-nitro-2-methylsulfonylphenylazo)-naphthol-1-phosphate and others which would be readily apparent to one skilled in the art, including those described in U.S. Pat. No. 4,983,512 (Techima et al). Preferably, the aryl phosphate ester is a naphthyl phosphate ester, and α-naphthyl phosphate esters are most preferred.

Many of the aryl phosphate esters are commercially available, or they can be prepared using known reagents and procedures such as by reacting the appropriate phenol or naphthol with phosphoryl chloride, removing the halogen and isolating the resulting phosphate ester.

The aryl phosphate ester is used in the form of a relatively nonhygroscopic salt. Generally such a salt has one or more divalent cations, such as alkaline earth cations (for example, magnesium and calcium). Preferably, calcium salts are used with the hemicalcium salt being most preferred. It is believed that the noted cations stabilize the phosphate ester by being less hygroscopic than sodium ion, and because of its ability to absorb water molecules, thereby keeping the portion of the phosphate ester which reacts relatively free from contact with water. The substrate is thus less likely to be hydrolyzed.

The diazonium and tetrazolium salts useful in the practice of this invention must be those capable of reacting with a phenol reaction product generated by the action of PAP on the substrate, to produce a chromophore at a pH in the range of from about 3 to about 6.5. A diazonium salt is generally an organic salt of a compound having a diazonium radical. Aromatic diazonium salts are preferred.

Particularly useful diazonium salts include, but are not limited to, those having the following structure:

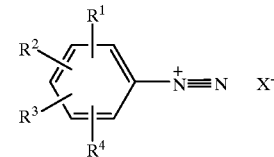

wherein $R^1$, $R^2$, $R^3$ and $R^4$ are independently hydrogen, halo (such as chloro, bromo or iodo), alkyl of 1 to 12 carbon atoms (such as methyl, ethyl, isopropyl, t-butyl, sec-butyl, n-butyl, pentyl, octyl, isononyl and dodecyl), nitro, cyano, alkoxy of 1 to 6 carbon atoms (such as methoxy, ethoxy, pentoxy, isopropoxy, t-butoxy and hexoxy), aryloxy of 6 to 10 carbon atoms in the aromatic ring, including aryloxy substituted with alkoxy and alkyl as defined above (such as phenoxy, naphthoxy, tolyloxy and p-nitrophenoxy), aryl of 6 to 10 carbon atoms (such as phenyl, naphthyl, -methylphenyl, m-ethoxyphenyl, p-cyanophenyl and o-methoxyphenyl), acyl of 1 to 12 carbon atoms (such as acetyl, propionyl, benzoyl and butyryl), and substituted or unsubstituted carbamoyl or sulfamoyl (such as carbamoyl, sulfamoyl, N,N-dimethylcarbamoyl and N,N-diethylsulfamoyl). Preferably, $R^1$, $R^2$, $R^3$ and $R^4$ are independently hydrogen, methyl, chloro, N,N-diethylsulfamoyl, nitro or methoxy.

In addition, any two of these radicals at adjacent positions on the ring can be taken together to represent an 6- to 10-membered fused aromatic ring system, including both heterocyclic or carbocyclic fused aromatic rings. Such rings can include carbon, nitrogen, oxygen or sulfur atoms in the ring structure. Preferably, 6- to 10-membered carbocyclic ring systems are formed in this manner.

It is understood that $R^1$, $R^2$, $R^3$ and $R^4$ are not any groups that could interfere either with the diazotization reaction used in the assay to provide a diazonium salt, or the coupling reaction used in the assay to effect azo dye formation.

In the salt noted above, $X^-$ represents any suitable anion such as halide (for example, chloride, bromide, fluoride and iodide), tetrafluoroborate, chlorozincate, hemizinc chloride, nitrate, perchlorate, p-toluenesulfonate and others readily apparent to one skilled in the art.

Representative useful diazonium salts include, but are not limited to, N',N'-diethyl-4-methoxymetanilamide diazonium salt (known as Fast Red-ITR salt), 4-chloro-2-methylbenzendiazonium salt (known as Fast Red TR salt), diazotized 2-methoxy-5-chloroaniline (known as Fast Red RC salt) and diazotized 5-nitro-2-amino-1-methoxybenzene (known as Fast Red B). The Fast Red TR salt is most preferred.

Tetrazolium salts are organic salts in which the organic portion contains one or two tetrazole rings, generally with aryl substituents at various positions. Tetrazolium salts having two tetrazole rings can be coupled so as to provide a diphenyl group with the tetrazole rings in the two para positions.

Many useful diazonium and tetrazolium compounds are described for example, in U.S. Pat. No. 3,905,872 (Forgione), U.S. Pat. No. 4,772,553 (Fujii et al), U.S. Pat. No. 4,892,817 (Pawlak) and U.S. Pat. No. 4,892,833 (Weiss et al) and Japanese Patent Publication 63/088,000 (published Apr. 19, 1988). Many diazonium and tetrazolium salts useful herein are available from a number of commercial sources, and those not readily available can be readily prepared by a skilled organic chemist using available reagents and known procedures.

The relatively nonhygroscopic aromatic phosphate substrate and diazonium or tetrazolium salt described above can be incorporated into the element of this invention in any suitable location. In the simplest embodiment, they are incorporated into the porous spreading zone (or layer) of a single-zoned element. In other embodiments containing a multiplicity of zones or layers, the noted reagents can be located together or separately in one or more of the zones. Preferably, they are in the same layer of a multilayer element.

The element also contains one or more buffers which maintains the element at a pH of from about 3 to about 6.5 during the assay. Useful buffers are well known in the art and include, for example, citrate, acetate, succinate, phthalate, glutaric and N-(2-acetamido)iminodiacetic, and the corresponding free acids. The buffers are preferably located in any of one or more zones of the element different from that zone containing the substrate. The element is preferably buffered to a pH of from about 4.5 to about 6.

It also is preferred that the element contain one or more accelerators which enhance the enzymatic reaction of the analyte and production of dye [see Saini et al, *J.Biol.Chem.*, 25(20), pages 10453–10455, 1981 and Buchwald et al, *J.Biol.Chem.*, 259(4), pages 2208–2213, 1984]. Such compounds are generally straight or branched chain diols having from 3 to 8 carbon atoms. They include, but are not limited to, 1,4-butanediol, 1,5-pentanediol, 1,2-propanediol, glycerol, 2,3-butanediol, 1,6-hexanediol, 1,5-hexanediol and others readily apparent to one skilled in the art. These accelerators are preferably in a zone other than the zone containing the substrate. Most preferably, the accelerators and buffers are in the same zone.

The elements can also contain one or more other addenda commonly included for manufacturing or operational advantages. Such addenda include surfactants, ion chelating agents, coating solvents, binders, hardeners, antioxidants and other materials readily apparent to one skilled in the art. Representative elements and their components are described in the examples below.

The amounts of reagents incorporated into the element of this invention are well within the skill of the ordinary worker in the art. More specifically, the aromatic phosphate substrate is generally present in an amount within the range of from about 0.005 to about 5 $g/m^2$ (dry weight), with an amount of from about 0.05 to about 1 $g/m^2$ being preferred. The diazonium or tetrazolium salt is generally present in an amount within the range of from about 0.005 to about 5 $g/m^2$ (dry weight), with an amount of from about 0.05 to about 3 $g/m^2$ being preferred. The accelerator, when used, is generally present in an amount within the range of from about 0.05 to about 10 $g/m^2$ (dry weight), with an amount of from about 0.5 to about 6 $g/m^2$ being preferred. The other addenda (including buffers and surfactants) are present in readily known or determinable amounts.

A variety of different elements, depending upon the method and equipment for assay, can be prepared in accordance with this invention. They can be configured in a variety of forms and shapes, including elongated tapes of any desired width, sheets, slides or chips. Preferred elements are configured as test slides like those commercially available under the EKTACHEM™ trademark for a variety of clinical assays. Such test slides are described in a considerable number of patents and other publications. Generally, the layers are formed on a suitable support by applying specific aqueous or solvent-based formulations of individual layer compositions in sequence using suitable coating equipment, and procedures followed by drying.

In a preferred embodiment, a multilayer analytical element of this invention comprises a nonporous, transparent support having thereon, in order and in fluid contact:

a reagent layer containing a suitable buffer as noted above, and a porous spreading layer containing the aromatic phosphate substrate and diazonium or tetrazolium salt as described above.

In an even more preferred embodiment, the reagent and porous spreading layers are separated by a hydrophilic subbing layer, such as a layer prepared from gelatin or other colloidal binder materials, vinyl pyrrolidone, acrylamide or N-alkyl-substituted acrylamide polymers (such as an N-isopropylacrylamide polymer), or other materials well known in the art.

The assay of this invention can be manual or automated. In general, the element is used by physically contacting it with the test specimen (for example from 1 to 200 $\mu l$) suspected of containing prostatic acid phosphatase under ambient conditions (although other temperatures can be used). The specimen and reagents become mixed within the one or more zones of the element and react to provide a dye. Contact can be achieved in any suitable manner, for example by dipping or immersing the element into the specimen or preferably, by spotting the specimen onto the element by hand, machine or suitable dispensing means.

After specimen application, the element is exposed to any conditioning, such as incubation, heating or otherwise, that may be desirable to quicken or otherwise facilitate obtaining a test result.

Generally within about 5 minutes, and preferably within about 3 minutes, a first spectrophotometric measurement is made of any chromophore formed in the element. Since PAP is an enzyme which reacts over time, generally a second measurement is taken a few minutes later to provide a rate response. Chromophore formation can be measured with suitable reflection or transmission spectrophotometric equipment and procedures as a measure of analyte activity and presence in the test sample.

The chromophore is generally measured at a wavelength which is within the range of from about 350 to about 800 nm depending upon the reactants used, with measurement at a wavelength of from about 400 to about 650 nm being preferred. Measuring at higher wavelengths, such as from about 550 to about 650 nm (most particularly at 600 nm), avoids interference from bilirubin.

The following examples are included to illustrate the practice of this invention, and are not meant to be limiting in any way. The materials used in the examples were obtained as follows:

ESTANE™ 5715 polyurethane resin from B.F. Goodrich,

TRITON™ X-405 nonionic surfactant from Rohm and Haas,

ZONYL FSN™ nonionic surfactant from DuPont, the α-naphthyl phosphates from American BioOrganics or Sigma Chemical Co., Fast Red TR salt from Sigma Chemical Co., and the remainder of the materials from Eastman Kodak Company or other commercial sources, or they were prepared using standard procedures and readily available starting materials.

As used herein, one I.U. represents the International Unit for enzyme activity and is defined as the amount of enzyme activity required to catalyze the conversion of 1 μmole of substrate to product per minute under standard pH and temperature conditions. For PAP, the standard conditions are 37° C. and a pH of about 5.4.

EXAMPLE 1

Multilayer Analytical Element for the Determination of Prostatic Acid Phosphatase and Comparative Elements The element illustrated below was prepared by formulating the materials of each layer into coating dispersions using known procedures and solvents, and coating them in the order shown using standard coating equipment and procedures. The element of this invention was compared in storage stability of the reagents (particularly the nonhygroscopic aromatic phosphate substrate) to the elements outside the present invention using hygroscopic aromatic phosphate substrates.

|  |  | Dry Layer Coverage (g/m$^2$) |
|---|---|---|
| Spreading Layer | Barium sulfate | 107.6 |
|  | Cellulose | 8.6 |
|  | acetate |  |
|  | TRITON™ X-405 surfactant | 2.1 |
|  | Fast Red TR salt | 0.7 |
|  | α-Naphthyl phosphate, hemicalcium salt | 0.4 |
|  | ESTANE™ polyurethane resin | 1.4 |
| Subbing Layer | Poly(N-isopropyl-acrylamide) | 0.4 |
| Reagent Layer | Gelatin | 12 |
|  | Citrate buffer (pH 5.5) | 5.5 |
|  | Bis (vinylsulfonylmethyl) ether hardener | 0.2 |
|  | 1,4-Butanediol | 1.8 |
|  | 1,5-Pentanediol | 4.0 |
|  | Poly (ethyleneterephthalate) Support |  |

Comparative elements were similarly prepared having the following substrates present in the spreading layer at the same coverage (0.4 g/m$^2$):

Comparative Element A: disodium salt of α-naphthyl phosphate,

Comparative Element B: monosodium salt of α-naphthyl phosphate, and

Comparative Element C: α-naphthyl phosphoric acid.

A sample (10 μl) of a buffered solution (20 mmolar citrate, pH 5.1) containing PAP (47 I.U./liter) was applied to each element, and the rate of dye development was measured by reflectance spectrophotometry. Each of the elements was then kept at 21° C. and 15% relative humidity for 1 week, and retested. The results of the two tests were compared to show the amount of loss of reagent stability as expressed in percent compared to an element used without room temperature storage.

| Element | Rate Loss |
|---|---|
| Example 1 | 0.2% |
| Comparative Element A | 6.6% |
| Comparative Element B | 1.7% |
| Comparative Element C | 1.5% |

EXAMPLE 2

Determination of Prostatic Acid Phosphatase

The element of Example 1 was used to detect prostatic acid phosphatase at various concentrations, and after several days of storage.

In one set of experiments, individual elements were contacted with a sample containing 13 I.U./liter of the analyte and the resulting dye development rate was measured at 600 nm to determine rate response using a conventional reflectance spectrophotometer after the conditioning noted below.

| Element | Rate Response | Percent of "Fresh Rate |
|---|---|---|
| Fresh* | 0.01293 | 100 |
| 7 days @ 25° C. | 0.01269 | 98.1 |
| 14 days @ 25° C. | 0.01258 | 97.3 |
| 21 days @ 25° C. | 0.01248 | 96.5 |
| 28 days @ 25° C. | 0.01223 | 94.6 |

*Used immediately without storage

These data indicate that the element of this invention is highly stable after storage at conditions typically found at a site of use.

Another set of experiments were carried out using a large number of elements like those of Example 1 to detect unknown amounts of prostatic acid phosphatase. The dye signal ($D_R$, reflectance density) formed in response to the analyte was measured and compared to the predicted value to determine precision of the assay. The results are shown in the following table.

TABLE

| PAP (I.U./l) | Number of Tests | Rate ($D_R$/min) | Predicted PAP (I.U./l) | Coefficient of Variation |
|---|---|---|---|---|
| 0.78 | 32 | 0.00082 | 0.74 | 6.5% |
| 1.1 | 187 | 0.00139 | 1.1 | 3.5% |
| 6.60 | 32 | 0.00743 | 6.58 | 2.4% |
| 13.7 | 32 | 0.01294 | 13.7 | 1.4 |
| 20.0 | 32 | 0.01725 | 20.0 | 1.8% |

EXAMPLE 3

Preferred Element

A preferred element of this invention was prepared having the following layer arrangement and components:

| | | Dry Layer Coverage (g/m$^2$) |
|---|---|---|
| Spreading Layer | Barium sulfate | 108.6 |
| | Cellulose acetate | 8.6 |
| | TRITON ™ X-405 surfactant | 2.1 |
| | Fast Red TR salt | 0.7 |
| | Hemicalcium α-naphthyl phosphate | 0.2 |
| | ESTANE ™ polyurethane resin | 1.4 |
| Subbing Layer | Poly(N-iso-propylacryl-amide) | 0.39 |
| Reagent Layer | Gelatin | 14 |
| | Sodium citrate buffer (pH 5.5) | 4.8 |
| | Citric acid | 0.71 |
| | Bis (vinylsulfon-ylmethyl) ether hardener | 0.2 |
| | 1,4-Butanediol | 1.8 |
| | 1,5-Pentanediol | 4.0 |
| | ZONYL ™ FSN nonionic surfactant | 0.2 |
| | Poly (ethylene-terephthalate) Support | |

EXAMPLE 4

Comparison of Elements with Diazonium Salt in Different Locations

This example compares the performance of an analytical element of this invention with one outside the scope of this invention whereby the diazonium salt is located in a layer other than the porous spreading layer.

The element of Example 1 was compared in the determination of PAP with the performance of a similar element whereby the Fast Red TR salt was located in the reagent layer. The dye development was evaluated at several concentrations of PAP using the procedure and equipment described in Example 1. The results are presented in the following Table. The rate responses were measured immediately after manufacture and a second time (identified as "aged") after storage at 21° C. and 15% relative humidity for four weeks.

| Concentration of | Rate Response* | | | |
|---|---|---|---|---|
| | Reagent Layer | | Spreading Layer | |
| PAP (I.U./liter) | Initial | "Aged" | Initial | "Aged" |
| 3 | 0.010 | 0.001 | 0.003 | 0.003 |
| 17 | 0.015 | 0.002 | 0.014 | 0.013 |
| 47 | 0.018 | 0.005 | 0.029 | 0.029 |

*Density change per minute

These results indicate that storage stability of the element was reduced when the diazonium salt was placed in the hydrophilic reagent layer containing the accelerators and buffer. Placement of the salt in the more hydrophobic spreading layer improves the storage stability of the element.

The invention has been described in detail with particular reference to preferred embodiments thereof, but it will be understood that variations and modifications can be effected within the spirit and scope of the invention. All patents, patent applications (published or unpublished, domestic or foreign), journal literature, books and other published prior art cited herein are incorporated herein by reference for the teaching therein pertinent to this invention.

We claim:

1. An analytical element useful for the determination of prostatic acid phosphatase in an aqueous specimen comprising:

a porous spreading zone containing
      (a) a nonhygroscopic aromatic phosphate which reacts as a substrate with prostatic acid phosphatase to produce a phenol reaction product, said nonhygroscopic aromatic phosphate substrate being an alkaline earth salt of an aryl phosphate ester, and
      (b) a diazonium or tetrazolium salt which is capable of reacting with said phenol reaction product to provide a chromophore,
   said element further comprising a buffer which maintains said element at a pH of from about 3 to about 6.5 when contacted with an aqueous specimen.

2. The element of claim 1 wherein said substrate is the hemicalcium salt of α-naphthyl phosphate ester.

3. The element of claim 1 wherein said diazonium salt has the structure:

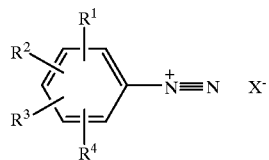

wherein $R^1$, $R^2$, $R^3$ and $R^4$ are independently hydrogen, halo, alkyl, nitro, cyano, alkoxy, aryloxy, aryl, acyl, carbamoyl or sulfamoyl, or any two of said radicals which are at adjacent positions on the aromatic ring can be taken together to form an 6- to 10-membered fused aromatic ring, and $X^-$ is an anion.

4. The element of claim 3 wherein $R^1$, $R^2$, $R^3$ and $R^4$ are independently hydrogen, methyl, chloro, nitro, N,N-diethylsulfamoyl or methoxy.

5. The element of claim 3 wherein said diazonium salt is N',N'-diethyl-4-methoxymetanilamide diazonium salt, 4-chloro-2-methylbenzendiazonium salt, diazotized 2-methoxy-5-chloroaniline or diazotized 5-nitro-2-amino-1-methoxybenzene.

6. The element of claim 5 wherein said diazonium salt is 4-chloro-2-methylbenzendiazonium salt.

7. The element of claim 1 wherein said porous spreading zone is a blush polymer spreading layer coated on a nonporous, transparent support.

8. A multilayer analytical element for the determination of prostatic acid phosphatase comprising a nonporous, transparent support having thereon, in order and in fluid contact:

a reagent layer containing a buffer which maintains said element at a pH of from about 3 to about 6.5 when contacted with an aqueous specimen, and a porous spreading layer containing
(a) a nonhygroscopic aromatic phosphate which reacts as a substrate with prostatic acid phosphatase to produce a phenol reaction product, said nonhygroscopic aromatic phosphate substrate being an alkaline earth salt of an aryl phosphate ester, and
(b) a diazonium or tetrazolium salt which is capable of reacting with said phenol reaction product to provide a chromophore.

9. The element of claim 8 wherein said substrate is hemicalcium salt of α-naphthyl phosphate ester, and said diazonium salt is 4-chloro-2-methylbenzendiazonium salt.

10. The element of claim 8 further comprising an accelerator in said reagent layer.

11. The element of claim 10 wherein said accelerator is 1,5-pentanediol, 1,4-butanediol, 1,2-propanediol, glycerol, 2,3-butanediol, 1,6-hexanediol or 1,5-hexanediol.

12. The element of claim 8 wherein said porous spreading layer is a blush polymer spreading layer, and said element further comprises a subbing layer between said spreading and reagent layers.

13. A method for the determination of prostatic acid phosphatase comprising the steps of:

A) contacting an aqueous specimen suspected of containing prostatic acid phosphatase with an analytical element comprising:
a porous spreading zone containing
(a) a nonhygroscopic aromatic phosphate which reacts as a substrate with prostatic acid phosphatase to produce a phenol reaction product, said nonhydroscopic aromatic phosphate substrate being an alkaline earth salt of an aryl phosphate ester, and
(b) a diazonium or tetrazolium salt which is capable of reacting with said phenol reaction product to provide a chromophore,
said element further comprising a buffer which maintains said element at a pH of from about 3 to about 6.5 during contact with said specimen, and B) detecting the formation of said chromophore as an indication of the presence of prostatic acid phosphatase in said specimen.

14. The method of claim 13 wherein said element comprises a buffer which maintains said element at a pH of from about 4.5 to about 6 during said method.

15. The method of claim 14 wherein said aqueous specimen is human serum or plasma.

16. The method of claim 13 wherein said element comprises a nonporous, transparent support having coated thereon in order and in fluid contact, a reagent layer, a subbing layer and said porous spreading zone which is a coated layer, and said buffer is located in said reagent layer.

17. The method of claim 13 wherein said chromophore is detected at a wavelength in the range of from about 550 to about 650 nm.

18. A method for providing a storage stable analytical element useful for the determination of prostatic acid phosphatase comprising:

A) applying a reagent layer formulation containing:
an accelerator, and
a buffer which maintains said element at a pH of from about 3 to about 6.5 when contacted with an aqueous specimen,
to a nonporous, transparent support, B) applying a subbing layer formulation to said reagent layer, and C) applying a porous spreading layer formulation to said subbing layer, said spreading layer containing
(a) a nonhygroscopic aromatic phosphate which reacts as a substrate with prostatic acid phosphatase to produce a phenol reaction product, said nonhydroscopic aromatic phosphate substrate being an alkaline earth salt of an aryl phosphate ester, and
(b) a diazonium or tetrazolium salt which is capable of reacting with said phenol reaction product to provide a chromophore.

* * * * *